(12) United States Patent
Shah

(10) Patent No.: US 6,805,857 B2
(45) Date of Patent: Oct. 19, 2004

(54) METHOD OF MODULATING FACTOR D, FACTOR H AND CD4 CELL IMMUNE RESPONSE WITH A POLYSTYRENE SULFONATE, ALGINATE, AND SALINE INFUSION SOLUTION

(76) Inventor: Kumarpal A. Shah, 28 Ridge Rd., Searington, NY (US) 11507

( * ) Notice: Subject to any disclaimer, the term of this patent is extended or adjusted under 35 U.S.C. 154(b) by 0 days.

(21) Appl. No.: 10/013,020

(22) Filed: Dec. 7, 2001

(65) Prior Publication Data

US 2004/0180055 A1 Sep. 16, 2004

Related U.S. Application Data

(63) Continuation-in-part of application No. 09/955,803, filed on Sep. 19, 2001, which is a continuation-in-part of application No. 09/519,229, filed on Mar. 6, 2000, now abandoned.

(51) Int. Cl.[7] .............................................. A61K 31/74
(52) U.S. Cl. ........................... 424/78.27; 424/78.08; 424/78.18; 424/78.17; 424/167.1; 424/489; 424/499; 424/501; 424/85.1; 424/85.2; 424/885; 424/451; 424/439; 424/442; 424/457; 514/458; 514/55; 514/57; 514/2
(58) Field of Search ..................... 514/458, 55, 57, 514/2, 885, 689; 424/439, 451, 442, 464, 468, 401, 85.1, 426, 85.2, 434, 499, 435, 469, 445, 482, 78.27, 78.08, 78.18, 78.17, 167, 489, 501, 885, 457, 78.1, 167.1, 78.35; 425/435, 436, 426, 428, 430, 464, 469, 499, 501, 497

(56) References Cited

U.S. PATENT DOCUMENTS

| | | | | |
|---|---|---|---|---|
| 4,764,603 A | * | 8/1988 | Zappia et al. ............... 536/27.3 |
| 4,871,352 A | * | 10/1989 | Tran ............................. 604/82 |
| 5,308,612 A | * | 5/1994 | Lee ........................... 424/78.35 |
| 5,585,106 A | * | 12/1996 | Gristina et al. ............. 424/401 |
| 5,837,444 A | | 11/1998 | Shah |
| 5,942,242 A | * | 8/1999 | Mizushima et al. ........ 424/434 |
| 5,976,780 A | | 11/1999 | Shah |
| 6,022,855 A | | 2/2000 | Thomas et al. |
| 6,028,115 A | * | 2/2000 | Zaneveld et al. ........... 514/709 |
| 6,239,182 B1 | * | 5/2001 | Zaneveld et al. ........... 514/764 |
| 6,270,755 B1 | * | 8/2001 | Bacon Kurtz et al. ... 424/78.08 |
| 6,290,946 B1 | * | 9/2001 | Kurtz et al. ............. 424/78.08 |
| 6,444,221 B1 | * | 9/2002 | Shapiro ...................... 424/451 |
| 6,517,826 B1 | * | 2/2003 | Kurtz et al. ............. 424/78.08 |
| 6,517,827 B1 | * | 2/2003 | Bacon Kurtz et al. ... 424/78.08 |
| 6,703,013 B1 | * | 3/2004 | Ninomiya et al. ......... 424/78.1 |
| 2001/0041171 A1 | * | 11/2001 | Kurtz et al. ............... 424/78.1 |
| 2003/0138397 A1 | * | 7/2003 | Kurtz et al. ............. 424/78.31 |

OTHER PUBLICATIONS

Betley, MJ et al, Biochemical and Biophysical Research communications, vol. 162(3), Aug. 15, 1989, pp. 1388–1395.*

(List continued on next page.)

Primary Examiner—Lynette R. F. Smith
Assistant Examiner—Ginny Allen Portner
(74) Attorney, Agent, or Firm—Keusey, Tutunjian & Bitetto, P.C.

(57) ABSTRACT

Anthrax bio-terrorism is a poor man's nuclear bomb with devastating effects on the freedom and economy of any nation. No nation is immune. Urgently, there is a need for life saving technology that can be readily available and deployed in real time. Polystyrene sulfonate is the answer. It is life saving and will help in the development of next generation superior vaccines.

14 Claims, 2 Drawing Sheets

Therapeutic Strategy
Anthrax Bioterrorism

OTHER PUBLICATIONS

Cotter, PA et al, Science, vol. 273, Aug. 30, 1996, pp. 1183–1185.*

Setoyama, H et al, Transplantation Proceedings, vol. 30, pp. 67–70, 1998, The potential of anticomplement synthetic sulfonic polymers for xenotransplantation.*

Smith, TA et al, new York State Journal of Pharmacy, V11 (3), pp. 74–75, 1991 (abstract only).*

Engel, LS et al, Japanese Journal of ophthalmology, 1996, vol. 40(2), pp. 212–219, (abstract only).*

Fogt, F, et akm Comment on Am. J. Surg. Pathol. Jan. 1997 vol. 21(1), pp. 60–69, Sodium polystyrene sulfonate damage (abstract only).*

Gerstman, BB et al, American J. of Kidney diseases–the official journla of the National Kidney Foundation, Aug. 1992, vol. 20(2), apges 159–161, Intestinal necrosis associated with postoperative orally administered sodium polystyrene sulfonate in sorbitol.*

Grube, B et al, Archives of Surgery, Jun. 1987, vol. 122, REad Before the 94th Annual meeting of the Western Surgical Association Dearborn, Mich., Nov. 16–Nov. 19, 1986, Clostridium difficile diarrhea in Critically III Burned Patients.*

Mogi, Y et al, Rinsho ketsueki the Japanese journal of clinical hematology, (Japan) Nov. 1997, ovl. 38(11), pp. 1224–1228, Thrombocytopenia associated with sodium polystyrene sulfonate, (abstract only).*

Schiere, S et al, Nederlands tijdschrift voor geeneskunde (Netherlands) Nov. 1., 1997, vol. 141(44) pp. 2127–2129, Sodium Polystyrene sulfonate (resonium A) as possible cause of rectal blood loss, (abstract only).*

Pascual, M et al, Biomaterials, Jul. 1993, vol. 14(3), pp. 664–670.*

Higaki, M et al, Vaccine, Apr. 1998, vol. 16(7), pp. 741–745.*

Moreau, JM et al, Current eye research, Aug. 1998, vol. 17(8), pp. 808–812.*

Herold, B et al, Rediatric Research, vol. 45(4 part 2), page 163A, Apr. 1999, Polystyrene sulfonate is a safe and effective candidate topical antimicrobial for the prevention of sexually transmitted diseases.*

Novello, A.C. "Dear Doctor letter with 6 attachments" Oct. 19, 2001.

Hensley, S. and Winslow, R. Drug Companies Contemplate New Role as 'Biodefense Contractors' Wall Street Journal, Nov. 12, 2001.

Martinez, B. "Anthrax Victim's Son Sues Kaiser Facility His Father Consulted" Wall Street Journal, Nov. 14, 2001.

Bhatnagar, R. and Batra, S. Anthrax Toxin. Crit Rev Microbiol. 2001; 27(3): 167–200.

Walport, M. J. Advances in Immunology: Complement: First of two parts. N Engl J Med. 2001; 344:1058–1066.

Pangburn, M. K. Alternate Pathway: Activation and regulation, the complement system. Edited by Rother K., Till G.O., and Hansch G.M. Springer, 1998, 93–115.

Antimicrobial Defenses, Chapter 19, Biochemical Pathways: An Atlas of Biochemistry and Molecular Biology. Edited by Michal, G. Willey J. Publication, 2000.

Sahu A. and Lambris J. Structure and biology of complement protein C3, a connecting link between innate and adaptive immunity. Immunological Reviews, 2001; 180: 35–48.

Kilpatrick J.M., Babu Y.S., Agrawal A. et al. Control of the Alternate Complement Pathways: Inhibition of Factor D, Controlling the Complement System: For Novel Drug Development. Edited by Mazarakis, H.: Swart, S.J., IBC Inc Publication. 1997: 13: 203–225.

Rustaggi P.K., Kilpatrick J.M., Niwas S. et al. Development of Novel Broad Spectrum Serine Protease Inhibitors for use as Anticoagulants: Chapter 15, Anticoagulant, Antithrombotics and Thrombolytic Therapeutics, IBC Inc. 1998; II–1924: 307–319.

Pangburn M.K. Review: Host recognition and target differentiation by Factor H, a regulator of the Alternative pathway of the complement, Immunopharmacology. 2000; 49: 149–157.

Zipfel P.F. et al. Mini Review: Factor H and disease: A complement Regulator Affects Vital Body Functions Molecular Immunology, 1999:36, 241–248.

Zipfel P.F. Complement Factor H: Physiology and Pathology, Semin Thromb Hemost, 2001; 27: 191–9.

Stoiber H., Kacani L., Speth C. et al. The Supportive role of complement in HIV pathogenesis. Immunological Reviews, 2001; 180:168–176.

Speth C., Kacani L., Dierich M. Complement receptors in HIV infections: Immunological Reviews, 1997; 159: 49–67.

Chaplin J.W. HIV Pathogenesis: gp 120–antibody complexes bind CD 4 and kill T4 cells–Immunotoxin therapy should prevent the progression of HIV to AIDS, Medical Hypotheses, 1999: 52(2):133–146.

Hewson T., Lone N., Moore M. et al. Review Article: Interactions of HIV–1 with antigen presenting cells, Immunology and cell biology, 1999; 77: 289–303.

Fearon D.T and Locksley R.M. Instructive role of innate immunity in the acquired immune responses. Science, 1996; 272: 50–54.

Reis e Sousa C., Sher A. Kaye P. The role of dendritic cells in the induction and regulation of immunity to microbial infection. Current Opinion in Immunology, 1999: 11; 392–399.

Bell D., Young J.W and Banchereau J. Dendritic cells. Advances in Immunology, 1999; 72: 255–324.

Vanholder R., Van LA. and Ringoir S. Clinical experience with polysulfone: 10 years. Clinical Nephrology, 1994; 42: S 13–S 20.

Setoyama H., Inoue K., Iwata H. et al. The Potential of Anti–Complement Synthetic Sulfonic Polymers for Xenotransplantation. Transplantation Proceedings, 1998; 30: 67–70.

Iwata H., Murakami Y., Ikada Y. Control of Complement activities for immunoisolation. Ann NY Acad Sci., 1999; 875:7–23.

Date I., Miyoshi Y., Ono T. et al. Preliminary report of polymer–encapsulated dopamine–secreting cell grafting into the brain. Cell Transplantation, 1996; 5: S17–S19.

Pascual M., Plastre O., Montdargent B. et al. Specific interactions of polystyrene biomaterials with Factor D of human complement. Biomaterials. 1993; 14: 665–670.

Parish C R., Low L., Warren H.S. et al. A Polyanionic Binding Site on the CD 4 molecule: Proximity to the HIV–gp 120 Binding Region, The J. Of Immunology 1990; 145: 1188–1195.

Higaki M., Takase T., Igarashi R. et al. Enhancement of immune response to intranasal influenza HA vaccine by micro particle resin. Vaccine, 1998; vol. 16 No. 7: 741–745.

Chaplin A. J. The use of histological techniques for the demonstration of ion exchange resins. J Clin Pathology, 1999; 52: 776–779.

Rhodes J., Chen H., Hall S.R et al. Therapeutic potentiation of the immune system by co–stimulatory Schiff base forming drugs. Nature, 1995; 377(6544): 71–75.

Dierich M.P., Stoiber H. and Clivio A.A "Complement–ary" AIDS vaccine, Nature Medicine, 1996; vol. 2, No. 2: 153–155.

Mohan P., Schols D., Baba M. et al. Sulfonic acid polymers as a new class of human immunodeficiency virus inhibitors, Antiviral Research, 1992; 18:139–150.

Tan G.T., Wickramsinghe A., Verma S. et al. Sulfonic acid polymers are potent inhibitors of HIV–1 induced cytopathogenicity and the reverse transcriptases of both HIV–1 and HIV–2. Biochimica et Biophysica Acta, 1993; 1181(2):183–188.

Anderson R A., Feathergill K., Diao X. et al. Evaluation of Poly(Styrene–4–Sulfonate) as a Preventive agent for Conception and Sexually transmitted diseases. J Androl 2000 Nov.–Dec.; 21(6): 862–875.

Herold B.C, Bourne N.. Marcellino D. et al. Poly (Styrene–4–Sulfonate): An Effecitve Candidate Topical Antimicrobial for the Prevention of Sexually Transmitted Diseases. J Inf Dis 2000; 181:770–773.

Gerstman B.B. and Platt R. Uses of sodium polystyrene sulfonate in sorbitol in the United States, 1985–89. A. J. of Kidney Dis., 1991:15, No. 5, 619–620.

Sodium polystyrene sulfonate, Martindale: The complete Drug Reference, 32nd edition, edited by Parfitt K., Pharmaceutical Press, 1999: 995–996.

Pinto L.A., Shearer G.A.M. and Blazevic V. Short Analytical Review: Immune–Based Approaches for Control of HIV infection and Viral–Induced immunopathogenesis. Clinical Immunology 2000: 97, No. 1:1–8.

Fontanarosa P.B., DeAngelis C.D. Editorial: Basic Science and Translational Research. JAMA, 2001; 285:2246.

Moreau J.M., Green L.C., Engel L.S. et al. Effectiveness of ciprofloxacillin–polystyrene sulfonate (PSS), ciprofloxacin and ofloxacin in a staphylococcus keratitis model., Curr Eye Res, 1998; 17(8):808–12.

Inaba S., Nibu K., Takano H. et al. Potassium adsorption filter for RBC transfusion: A phase iii clinical trial. Transfusion, 2000; 40: 1469–1474.

Food and Drug Administration, HHS, Part 312–Investigational New Drug Application.

* cited by examiner

FIG. 1
Short Circuit of Immune System
Mechanism of Septic Shock

FIG. 2:
Therapeutic Strategy
Anthrax Bioterrorism

METHOD OF MODULATING FACTOR D, FACTOR H AND CD4 CELL IMMUNE RESPONSE WITH A POLYSTYRENE SULFONATE, ALGINATE, AND SALINE INFUSION SOLUTION

CROSS REFERENCE TO RELATED APPLICATIONS

The present application is continuation-in-part of co-pending U.S. patent application Ser. No. 09/955,803 entitled "Immune Modulation With Polystyrene Sulfonate" filed on Sep. 19, 2001, which is a continuation-in-part of U.S. patent application Ser. No. 09/519,229, entitled "Method for Immune Switching" filed on Mar. 6, 2000, now abandoned.

BACKGROUND OF THE INVENTION

1. Technical Field

This invention is related to emergency medical preparedness against anthrax bio-terrorism. More particularly, the present invention details a treatment and therapy for anthrax that sharply reduces the risk of mortality with "Zero" tolerance for time.

2. Description of Related Art

In a typical patient with inhalation anthrax, the onset of illness begins with flu-like symptoms and may include fever, malaise, cough and chest discomfort. However, unlike the flu, patients with inhalation anthrax rapidly progress downhill with acute symptoms of respiratory distress and tightening in the chest with constricting sensations. Fever, septic shock and death may soon follow within a span of 3–5 days. According to the consensus document published on anthrax bio-terrorism in 1999, the strategic release of anthrax spores in a large metropolitan city could cause the death of 130,000 to 3 million people. The medical cost is estimated to be 26.2 billion dollars per 100,000 cases, (Novello, A. C. "Dear Doctor letter with 6 attachments" Oct. 19, 2001). This worst-case scenario is due to the high (80–90%) mortality from the inhalation form of anthrax even with state of the art medical care.

In anthrax bio-terrorism, the major cause of concern is the risk of high mortality in the evolving medical war scenario at an international level, it is practically impossible to predict the magnitude and scale of bio-terrorist's operation. It is also not possible to predict where and when anthrax will strike. Urgently, therefore, there is a need for life saving technology that can be deployed globally in real time to reduce the immediate risk of mass murders by a bio-terrorist. Such a technology will be life saving both for the military and civilian defenses and would result in saving billions of dollars for the government. Current industry standard estimates for new drug development is 10–15 years at a cost of over $500 million. Anthrax illness in natural settings is rare. In its bio-terrorism form, its magnitude of problems and timing of attacks are unpredictable. Under this scenario, the current efforts to develop bio-defense industry with a proposed cost estimate of $50 billion doesn't address the critical needs of country's defense in real time. (Hensley, S. and Winslow, R. "Drug Companies Contemplate New Role as Biodefense Contractors" Wall Street Journal, Nov. 12, 2001).

The current state of the art public health guidance letters are based on what is known about anthrax bio-terrorism in its short history since the first week of October 2001. (Novello, A. C. "Dear Doctor letter with 6 attachments" Oct. 19, 2001). The guidance document to practicing physicians is the result of epidemiological findings done by the stale department. The guidance document's relevance to the medical management of "Life and Death matter with Inhalation anthrax" is that it has been a fertile ground for medical malpractice involving $37 million lawsuit in Maryland. (Martinez, B. "Anthrax Victim's Son Sues Kaiser Facility His Father Consulted" Wall Street Journal, Nov. 14, 2001).

Anthrax bacillus is an aerobic, Gram-positive organism. The virulence of the bacteria is related to the following critical factors:

1. The capsule: The capsule of anthrax bacilli contains polypeptide of D-glutamic acid. This is unusual. Most gram-positive or grain-negative bacteria capsules have polysaccharides or carbohydrate elements. The unusual nature of the capsule allows bacilli to survive externally, in harsh environmental conditions for decades. Anthrax bacillus infection is not transmitted from patient to healthy person. Yet, the free-floating state in the aerosolized form is extremely dangerous. Subjects are exposed to repeat or fresh infections. Decontamination procedures are extremely cost ineffective over a long period of time. If the area in which contamination occurs involves a large area or a city, its abandonment and sealing is required. Internally, in the living body the capsule facilitates bacterial infection by evading immune responses and resisting phagocytosis inside macrophages. Anti-microbial therapy is not associated with immunity. There is thus a delayed risk of relapse. To reduce the magnitude of these problems cost effective vaccine therapy that is directed to protect against the capsular antigen is needed. In future vaccine strategy, the need to address the problem of immune evasion and the resistance to phagocytosis is emphasized. (Novello, A. C. "Dear Doctor letter with 6 attachments" Oct. 19, 2001).

2. Macrophage: ace inside macrophages, bacilli multiply rapidly secreting polypeptide or proteins that have toxin-like properties. The amino acid composition of the three proteins synthesized by anthrax bacilli lacks a cysteine molecule; therefore they must maintain function in an oxidizing milieu. Macrophage is a preferred home because of its ability to form large amount of reactive oxygen intermediates (ROI). In the early stage, macrophage responds by stock piling large amount of inflammatory cytokines such as TNF Alfa and IL-1B. In the later stage, macrophages burst open and liberate large amounts of inflammatory cytokines. This leads to characteristic high mortality of the host due to sudden septic shock. (Bhatnagar, R and Batra, S. Anthrax Toxin. Crit Rev Microbiol. 2001; 27(3): 167–200).

3. The toxin: In anthrax infection three different types of proteins with toxin like properties are secrete& Synthesis of Protective antigen (PA) is critical. This protein As combines with other synthesized proteins such as Edema factor (EF) and/or Lethal factor (LF) to impart its toxicity. PA also binds with cell receptor of the host cell. It is clipped by host tissue serine proteases such as chymotrypsin and furin to PA 63. PA 63 facilitates the translocation of EF and LF in to the cytosol. Toxin manifests its cytotoxic effects in the cytoplasm. Thus formation of membrane attack complex on the self or host tissues and its translocation inside cells is critical before toxic effects of proteins is manifested. Appropriate vaccine strategy involving PA is expected to provide effective immune defenses against mortality due to toxins. EF is also a factor that is involved in immune evasion. Therefore, in future vaccine strategy, the problem of immune evasion should be addressed. (Novello, A. C. "Dear Doctor letter with 6 attachments" Oct. 19, 2001; Bhatnagar, R. and Batra, S. Anthrax Toxin. Crit Rev Microbiol. 2001; 27(3): 167–200).

The key to the understanding of anthrax pathogenesis is the working of the human defense system. The New England Journal of Medicine published a complex series of articles under the title "Recent Advances of Immunology" from July 2000. Based on this and other reference documents (Walport, M. J. Advances in Immunology: Complement: First of two parts. N Engl J Med. 2001; 344:1058–1066; Pangbum, M. K Alternate Pathway: Activation and regulation, the complement system. Edited by Rother K., Till G. O., and Hansch G. M. Springer, 1998, 93–115; Antimicrobial Defenses, Chapter 19, Biochemical Pathways: An Atlas of Biochemistry and Molecular Biology. Edited by Michal, G. Willey J. Publication, 2000; Sahu A. and Lambris J. Structure and biology of complement protein C3, a connecting link between innate and adaptive immunity. Immunological Reviews, 2001, 180: 35–48; Kilpatrick J. M., Babu Y. S., Agrawal A. et al. Control of the Alternate Complement Pathways: inhibition of Factor D, Controlling the Complement System: For Novel Drug Development. Edited by Mazarakis, H., Swart, S. J., IBC Inc Publication. 1997, 13: 203–225; Rustaggi P. K., Kilpatrick J. M., Niwas S. et al. Development of Novel Broad Spectrum Serine Protease Inhibitors for use as Anticoagulants: Chapter 15, Anticoagulant, Antithrombotics and Thrombolytic Therapeutics, IBC Inc. 1998; II-1924: 307–319; Pangburn M. K. Review: Host recognition and target differentiation by Factor H, a regulator of the Alternative pathway of the complement, lmmunopharmacology. 2000, 49:149–157; Zipfel P. F. et al. Mini Review: Factor H and disease: A complement Regulator Affects Vital Body Functions. Molecular Immunology, 1999: 36, 241–248; Zipfel P. F. Complement Factor H: Physiology and Pathology, Semin Thromb Hemost, 2001, 27: 191–9; Stoiber H., Kacani L., Speth C. et al. The Supportive role of complement in HIV pathogenesis. mmunological Reviews, 2001, 180:168–176; Speth C., Kacani L., Dierich M. Complement receptors in HIV infections: immunuological Reviews, 1997, 159: 49–67; Chaplin J. W. HIV Pathogenesis: gp 120-antibody complexes bind CD 4 and kill T4 cells-immunotoxin therapy should prevent the progression of HIV to AIDS, Medical Hypotheses, 1999, 52(2):133–146; Hewson T., Lone N., Moore M. et al. Review Article: Interactions of HIV-1 with antigen presenting cells, Immunology and cell biology, 1999, 77: 289–303; Fearon D. T and Locksley R. M. Instructive role of innate immunity in the acquired immune responses. Science, 1996, 272: 50–54; Reis e Sousa C., Sher A. Kaye P. The role of dendritic cells in the induction and relation of immunity to microbial infection. Current Opinion in Immunology, 1999: 11: 392–399; Bell D., Young J. W and Banchereau J. Dendritic cells. Advances in Immunology, 1999, 72: 255–324), the working of the human defense system can be simplified. The human defense system comprises the following three levels of hierarchical organization:
1. The first level of hierarchy is determined by an ancient anti-microbial system such as the complement system. April 2001 issue of New England Journal of medicine summarizes the current state of the art understanding of the complement system. (Walport, M. J. Advances in Immunology: Complement: First of two parts. N Engl J Med. 2001; 344:1058–1066). A critical feature of this article is the summary of the recent state-of-the-art explanation as to how the complement system is directed to foreign pathogens without harming the host. The relationship of complement proteins such as Factor D and Factor H is explained. The fact of critical importance in this relationship is the new emerging role of Factor H in protecting the self or host tissue and regulating the actions of Factor D or controlling the non-self responses directed against foreign pathogens. In the first level of hierarchy, the non-self identity or foreignness of pathogen is determined by a carbohydrate signature that is carried by pathogens. Complement system is particularly activated to contain foreign intrusion. This involves flagging of pathogens as foreign with C3 convertase and forming membrane attack complex to cause initial damage to pathogens.
2. The second level of hierarchy is defined by CD 4 cells. CD 4 cells are present on monocytes, macrophages and antigen presenting cells. The intermediary products of the activated complement system, such as C3a–C5a, attract CD 4 cells to the site of foreign pathogens. Surface receptors of CD 4 cells, such as CD 4 receptors, CR1 to CR3, FcyR and chemokine receptors, help facilitate the entry of pathogen fragments inside cells. The fragmented pathogens are taken up and are processed by phagocytosis for further breakdown. The final small foreign peptides are deposited in the grooves of MHC 1 and MHC 11. The second level of hierarchy is thus defined by a peptide signature. The foreign presence of pathogen is sensed in accordance to "Two signal hypothesis". In moving to the second level of hierarchy, the immune system loses its ability to identify carbohydrate signature.
3. The third level of hierarchy is determined by the cognate interactions between CD 4 and T cells. T cells may involve CD 4 T and/or CD 8T cells. This primes the adaptive immune system for clonal expansion, effector immune responses and the generation of memory responses. In the case of a repeat intrusion by a foreign invader, memory cells bypass the three levels of hierarchy and directly respond to provide vaccine responses. In the initial intrusion, pathogens are required to be processed by the three levels of hierarchical system in order.

Bacteria and viruses co-evolved with human existence. They constantly fight with human defenses for their survival advantages. In recent years, particularly since 1993–94, a large number of bacteria, viruses, parasites and cancer cells were identified that pirates the hierarchical functioning of the human defense system for its own survival advantage. This list is growing. Streptococcus pyogenes, Borerelia burgdorferi, Neisseria gonorrheas, N. meningitides, Yersinia enterocolitica, Echinococcus granulosus, Onchocerca volvulus, HIV, and certain cancers such as glioblastoma, bladder cancer and transitional carcinoma are examples which exploit the working of Factor H or its related proteins. C3 convertase and its breakdown products act as intermediaries and are downstream effects of Factor H action. They act as opinion and facilitate the entry of pathogens inside CD 4 cells. CD 4 receptors, CR1 to CR3 complement receptors, chemokine receptors and FcyR receptors variably work to gather and facilitate the entry of foreign pathogens inside CD 4 cells. Epstein-Barr virus, HIV and West Nile virus exploit the function of complement receptors such as CR1–CR3. Mycobacterium tuberculosis also exploits the working of CR3. (Walport, M. J. Advances in immunology: Complement: First of two parts. N Engl J Med. 2001, 344:1058–1066; Zipfel P. F. et al. Mini Review: Factor H and disease: A complement Regulator Affects Vital Body Functions. Molecular Immunology, 1999: 36, 241–248; Zipfel P. F. Complement Factor H: Physiology and Pathology, Serin Thromb Hemost, 2001, 27: 191–9). Many of these pathogens mask their identity as self by binding with Factor H. The Factor H on the surface of pathogens acts as a shield that protects it against activated complement system. C3 convertase is unable to form membrane attack complex and activated complement products C3a–C5a results in host inflammation. Factor H breaks down C3 convertase on the surface of pathogens and uses these products as opinion to gain entry or to facilitate the bacterial infection inside CD 4 cells. Once inside these cells, pathogens multiply and either bud out enveloping host cell membrane as in the case of viruses or are released in the blood stream or tissues due to cytolysis as in the case of bacteria to repeat the process of infection. This prevents the development of adaptive immunity. In cases of anthrax pathogenesis, immune evasion permits entry inside macrophages. The bacteria multiply and generate large amounts of toxins and inflammatory mediators. Complement system is persistently activated either due to bacteria, toxins and inflammatory mediators or host tissue damage, leading to septic shock and death. This permits the short-circuiting of the immune system and effective immune responses are not generated.

U.S. Pat. No. 6,290,946 B1 issued to Kurtz et al. on Sep. 18, 2001 (Kurtz et al. "Anionic Polymers as Toxin Binders and Antibacterial Agents", U.S. Pat. No. 6,290,946 B1) details the anionic polymers as toxin binders and antibacterial agents. The patent describes a method of inhibiting a toxin. The toxin is, typically, an exotoxin secreted by pathogenic microorganism, such as bacterium. The reference example of the disease model was antibiotic-associated colitis involving C. Difficile. The preferred method of therapy involved the use of poly (styrene sulfonate) and its analogs. Polystyrene sulfonate (PSS) has been studied in the basic science literature for its inhibitory actions on Factor D, Factor H and CD 4 cells. (Vanholder R., Van L. A. and Ringoir S. Clinical experience with polysulfone: 10 years. Clinical Nephrology, 1994, 42: S 13-S 20; Setoyama H., Inoue K., Iwata H. et al. The Potential of Anti-Complement Synthetic Sulfonic Polymers for Xenotransplantation. Transplantation Proceedings, 1998, 30: 67–70; Iwata H., Murakami Y., Ikada Y. Control of complement activities for immunoisolation. Ann NY Acad Sci., 1999, 875:7–23; Date L, Miyoshi Y., Ono T. et al. Preliminary report of polymer-encapsulated dopamine-secreting cell grafting into the brain. Cell Transplantation, 1996, 5: S17–S19; Pascual M., Plastre O., Montdargent B. et al. Specific interactions of polystyrene biomaterials with Factor D of human complement. Biomaterials. 1993, 14: 665–670; Parish C R., Low L., Warren H. S. et al. A Polyanionic Binding Site on the CD 4 molecule: Proximity to the HIV-gp 120 Binding Region, The J. Of Immunology 1990, 145: 1188–1195). It is also studied for its capacity to induce vaccine like responses (Higaki M., Takase T., Igarashi R. et al. Enhancement of immune response to intranasal influenza HA vaccine by micro particle resin. Vaccine, 1998, Vol. 16 No. 7: 741–745; Chaplin A. J. The use of histological techniques for the demonstration of ion exchange resins. J Clin Pathology, 1999, 52: 776–779; Rhodes J., Chen H., Hall S. R et al. Therapeutic potentiation of the immune system by co-stimulatory Schiff base forming drugs. Nature, 1995, 377(6544): 71–75; Dierich M. P., Stoiber H. and Clivio A. A "Complement-ary" AIDS vaccine, Nature Medicine, 1996, Vol. 2, No. 2: 153–155), as well as for its anti-microbial effects (Lee J. J. Use of polystyrene sulfonate and related compounds as inhibitors of Transactivating transcription factor (Tat) and therapeutics for HIV infection and AIDS. (1994) U.S. Pat. No. 5,308,612; Mohan P., Schols D., Baba M. et al. Sulfonic acid polymers as a new class of human immunodeficiency virus inhibitors, Antiviral Research, 1992, 18:139–150; Tan G. T., Wickramsinghe A, Verma S. et al. Sulfonic acid polymers are potent inhibitors of HIV-1 induced cytopathogenicity and the reverse transcriptases of both HIV-1 and HIV-2. Biochimica et Biophysica Acta, 1993, 1181(2):183–188; Anderson R A., Feathergill K., Diao X. et al. Evaluation of Poly(Styrene-4-Sulfonate) as a Preventive agent for Conception and Sexually transmitted diseases. J Androl 2000 November–December: 21(6): 862–875; Herold B. C, Bourne N.. Marcellino D. et al. Poly (Styrene-4-Sulfonate): An Effective Candidate Topical Antimicrobial for the Prevention of Sexually Transmitted Diseases. J Inf Dis 2000: 181:770–773).

Since 1994, we have been actively working in analyzing the effects of polystyrene sulfonate in relation to recent advances of immunology (K. Shah. "Islet Cell Transplant Machine For the Cure of Diabetes" U.S. Pat. No. 5,837,444; K. Shahl "Encapsulated Cell Device" U.S. Pat. No. 5,976, 780). Further, we have the first hand experience of using polystyrene sulfonate as a drug in the medical practice since 1975. (Gerstman B. B. and Platt R. Uses of sodium polystyrene sulfonate in sorbitol in the United States, 1985–89. A. J. of Kidney Dis., 1991:15, No. 5, 619–620; Sodium polystyrene sulfonate, Martindale: The complete Drug Reference, $32^{nd}$ edition, edited by Parfitt K., Pharmaceutical Press, 1999: 995–996). Below, based on our prior art experience and our patents related to PSS, the experimental data is briefly summarized:

A) Factor D inhibition: Several investigators have reported the complement inhibitory properties of PSS. This knowledge has been applied successfully to develop polysulfone and biosulfane hollow fibers for hemodialysis. The successful application of this advance in clinical medicine has been reported in the literature. (Vanholder R., Van L. A. and Ringoir S. Clinical experience with polysulfone: 10 years. Clinical Nephrology, 1994; 42: S13–S20). Another application of complement inhibition reported is cellular xenotransplant in diabetes and Parkinson's disease. The successful application of this advance in small animals has been reported. (Setoyama H., Inoue K., Iwata H. et al. The Potential of Anti-Complement Synthetic Sulfonic Polymers for Xenotransplantation. Transplantation Proceedings, 1998, 30: 67–70; Iwata H., Murakami Y., Ikada Y. Control of complement activities for immunoisolation. Ann NY Acad Sci., 1999, 875:7–23; Date I., Miyoshi Y., Ono T. et al. Preliminary report of polymer-encapsulated dopamine-secreting cell grafting into the brain. Cell Transplantation, 1996, 5: S17–S19).

The principle mechanism of complement inhibition is Factor D. (Pascual M., Plastre O., Montdargent B. et al. Specific interactions of polystyrene biomaterials with Factor D of human complement. Biomaterials. 1993; 14: 665–670). Other Factor D inhibitors in the literature also shown to be cross inhibitors of serine proteases such as involved in classical and lectin based pathways. (Kilpatrick J. M., Babu Y. S., Agrawal A. et al. Control of the Alternate Complement Pathways: Inhibition of Factor D, Controlling the Complement System: For Novel Drug Development. Edited by Mazarakis, H.; Swart, S. J., BC Inc Publication. 1997, 13: 203–225; Rustaggi P. K., Kilpatrick J. M., Niwas S. et al. Development of Novel Broad Spectrum Serine Protease Inhibitors for use as Anticoagulants: Chapter 15, Anticoagulant, Antithrombotics and Thrombolytic Therapeutics, BC Inc. 1998; II-1924: 307–319).

PSS is thus a serine protease inhibitor of chymotrypsin and furin proteases that are involved in the clipping of PA. U.S. Pat. No. 6,022,855 issued to Thomas et. al on Feb. 8, 2000 (Thomas et al. "Methods and Reagents for Inhibiting Furin Endoprotease", U.S. Pat. No. 6,022,855) details the role of serine protease inhibitors, such as alfal antitrypsin and its variant. This drug is used as a method for inhibiting the activity of furin endoprotease. Furin endoprotease is involved in the exocytotic secretary pathway of Golgi apparatus of the cells. Its function is to clip large inactive polypeptide or protein to shorter active peptides before they are liberated in the circulation. As shown in the pathogenesis of anthrax, ability of peptides secreted by anthrax assumes its toxic role only after PA is clipped by chymotrypsin and furin proteases at tissue level and PA 63 is translocated to the cytoplasm. PSS thus inhibits toxins in the blood as per U.S. Pat. No. 6,290,946 B1 and at tissue level before cellular entry. Inhibition of inflammatory complement products is yet another mode of action disclosed by this patent.

B. Factor H Inhibition: A curious observation made by Pascual et al. in 1993 (Pascual M., Plastre O., Montdargent B. et al. Specific interactions of polystyrene biomaterials with Factor D of human complement. Biomaterials. 1993; 14: 665–670) was the conflicting finding that the drug PSS leads to initial complement activation in spite of Factor D binding. They studied this phenomenon in detail and found it was due to Factor H binding which is twice as strong as Factor D binding. Factor H is a complement regulator protein. Its role at the time of the article was not clear. The subsequent recent advances in immunology have identified the importance of Factor H in the self-recognition of the host. This is an important protective mechanism to prevent indiscriminate activation of the complement system. The Factor H or its subsequent actions on Complement receptors are immune pirated by a large number of bacteria and viruses. The finding that Factor H is strongly inhibited by PSS is a discovery that is a predated medical advance whose therapeutic potential remains to be explored. (Walport, M. J. Advances in Immunology: Complement: First of two parts. N Engl J Med. 2001, 344:1058–1066; Pangburn M. K. Review: Host recognition and target differentiation by Factor H, a regulator of the Alternative pathway of the complement, Immunopharmacology. 2000, 49: 149–157; Zipfel P. F. et al. Mini Review: Factor H and disease: A complement Regulator Affects Vital Body Functions. Molecular Immunology, 1999: 36, 241–248). In anthrax pathogenesis, presence of capsular proteins and its immune evasion properties suggest the working of Factor H to facilitate bacterial infection inside CD 4 cells. Factor H blockage will prevent this immune piracy.

C. CD 4 Inhibition: CD 4 receptors are present on monocytes, macrophages and dendritic cells of innate immunity. Recent advances have identified the role of CD 4 receptors and its coordinated working with chemokine receptors such as CCCR 5 and CXCR 4 for microbial entry. Complement receptors CR 1 to CR3 and FcyR receptors may co-participate in the process. Such entry of microbes inside CD 4 cells leads to multiplication and budding out of fresh microbes. (Hewson T., Lone N., Moore M. et al. Review Article: Interactions of HIV-1 with antigen presenting cells, Immunology and cell biology, 1999, 77: 289–303). PSS binds to polyanionic binding site on CD 4 cells and inhibit microbial attachment to the surface of CD 4 cells. (Parish C R., Low L., Warren H. S. et al. A Polyanionic Binding Site on the CD 4 molecule: Proximity to the HIV-gp 120 Binding Region, The J. Of Immunology 1990, 145: 1188–1195; Mohan P., Schols D., Baba M. et al. Sulfonic acid polymers as a new class of human immunodeficiency virus inhibitors, Antiviral Research, 1992, 18:139–150; Tan G. T., Wickramsinghe A., Verma S. et al. Sulfonic acid polymers are potent inhibitors of HIV-1 induced cytopathogenicity and the reverse transcriptases of both HIV-1 and HIV-2. Biochimica et Biophysica Acta, 1993; 1181(2) :183–188). This prevents microbial entry inside cells. Factor H and CD 4 mechanisms coordinate immune evasion mechanisms of a number of bacteria and viruses.

D. Vaccine Responses: Immunization with Flu vaccine in infected patients seems to have cytotoxic properties. (Pinto L. A., Shearer G. A. M. and Blazevic V. Short Analytical Review: Immune-Based Approaches for Control of HW infection and Viral-Induced immunopathogenesis. Clinical Immunology, 2000; 97, No. 1:1–8). The strong humeral antibody responses (Th2) have been reported when flu vaccine is combined with PSS and administered nasally. (Higaki M., Takase T., Igarashi R. et al. Enhancement of immune response to intranasal influenza HA vaccine by micro particle resin. Vaccine, 1998; Vol. 16 No. 7: 741–745). PSS is a Schiff positive drug. (Chaplin A. J. The use of histological techniques for the demonstration of ion exchange resins. J Clin Pathology, 1999; 52: 776–779). Several small molecular weight substances that are Schiff positive react with CD 4 T (Th 0) cells of adaptive immunity. CD 4 T cells interact with CD 4 (matured dendritic cells) to stimulate (Th 1) cytotoxic responses. (Rhodes J., Chen H., Hall S. R et al. Therapeutic potentiation of the immune system by co-stimulatory Schiff base forming drugs. Nature, 1995; 377(6544): 71–75). As outlined before, Factor H, CD 4 cells, CD 4 T cells and Memory responses are hierarchical responses that require coordinated working. A number of bacteria and viruses disrupt the coordinated working of the immune system and prevent the successful generation of immune responses. PSS at Factor H level acts as a complementary vaccine by thwarting immune evasion mechanism. (Dierich M. P., Stoiber H. and Clivio A. A "Complementary" AIDS vaccine, Nature Medicine, 1996; Vol. 2, No. 2: 153–155). It has the capacity to generate humeral and cytotoxic immune responses by stimulating interaction of innate CD 4 (matured dendtitic cells) and CD 4 T cells. Thus, combining appropriate doses of PSS in currently evolved vaccines will improve their potential to generate appropriate vaccine responses. Vaccine responses take two to three weeks. There is a need to generate vaccine responses ultra-fast in anthrax. Further, vaccine studies need to follow ethical guidelines. Accordingly, there is a need for an efficient and effective therapeutic strategy for treating infections such as anthrax which reduces the incidence of mortality, is readily deployable in global settings with "zero" tolerance for time, and stimulates the immune system while keeping in line with ethical guidelines for vaccine studies. A therapeutic strategy as defined by the present invention facilitates this process.

SUMMARY OF INVENTION

The present invention is directed to a method for the treatment and therapy of anthrax that sharply reduces the risk of mortality and its related malpractice problems.

It is an object of the invention to provide a method for therapy that is cost effective and readily deployable in global settings with "Zero" tolerance for time.

It is yet another object of the invention to combine the method of therapy with an anti-microbial to obviate the prior art problem in which using anti-microbials does not provide immunity.

It is yet another object of the invention to inhibit harmful inflammatory host tissue responses as a result of anthrax pathogenesis.

It is further object of the invention to prevent immune evasion of bacteria and block the entry of anthrax entry inside macrophages.

It is yet another object of the invention to stimulate adaptive immune systems in an ultra-fast manner to stimulate humeral and cellular cytotoxic immune responses while keeping in line with ethical guidelines for vaccine studies.

It is the ultimate object of the invention to therapeutically reprogram the immune system in fatal infections such as anthrax.

In one aspect of the present invention, a method of treating infections in a mammal is provided comprising administering an effective amount of a pharmaceutical composition, said composition comprising polystyrene sulfonate and a therapeutic compound.

In another aspect of the present invention, a method of treating infections in a mammal is provided comprising administering a sufficient dosage of a pharmaceutical composition, said composition comprising polystyrene sulfonate and a vaccine.

In yet another aspect of the present invention, a method for enabling immune modulation therapy is provided using a pharmaceutical composition comprising polystyrene sulfonate to target Factor D, Factor H and CD4 cells.

In yet another aspect of the present invention, a method of treating immunity-related medical diseases in a mammal is provided comprising therapeutically reprogramming an immune system by administering an effective amount of polystyrene sulfonate to modulate an organic compound selected from the group consisting of Factor D, Factor H or CD 4 cells, and combinations thereof.

These and other aspects, features and advantages of the present invention will be described or become apparent from the following detailed description of the preferred embodiments, which is to be read in connection with the accompanying drawings.

The above objects of the present invention are achieved with reference to commonly assigned U.S. patent application Ser. No. 09/955,803 entitled "Immune modulation with polystyrene sulfonate" filed on Sep. 19, 2001, the disclosure of which is incorporated by reference. The review of that application in the light of anthrax pathogenesis and its current problems is done. From Bench to Bedside, from Concept to Clinical application, and from Discovery to Dissemination, translating novel scientific insights into new approaches for prevention, diagnosis, and treatment of diseases is the ultimate goal of medical research. Advances in medical research are based on the foundation work lead-out by basic science researchers. Its application to clinical science requires translational research processing. This requires reinterpretation of basic science data in the light of changes in the basic concepts of science. (Fontanarosa P. B., DeAngelis C. D. Editorial: Basic Science and Translational Research. JAMA, 2001; 285:2246). PSS is a drug that has been researched by a large number of investigators for its immune modulating potentials. When reexamined from the point of view of current knowledge of anthrax pathogenesis and problems posed it provides verification of basic hypotheses and observation with in-vitro studies and help advance the drug to define new therapeutic application for the prophylaxis and therapy in anthrax.

BRIEF DESCRIPTION OF THE DRAWINGS

FIG. 1 explains how anthrax pathogenesis short-circuits the innate immune responses to cause septic shock and death.

FIG. 2 defines an exemplary therapeutic strategy according to an aspect of the present invention where PSS is combined with an anti-microbial to provide five fold targeting of anthrax in which anti-microbial action is combined with immune modulation leading to therapeutic reprogramming of the immune system.

DETAILED DESCRIPTION OF PREFERRED EMBODIMENTS

FIG. 1 is an exemplary diagram illustrating how anthrax interacts with Factor D and Factor H and modulates their breakdown products to facilitate its surface entry in CD 4 macrophages. Once inside CD 4 cells, the anthrax bacteria rapidly multiplies, prevents generation of effective immune responses, and causes liberation of large amounts of toxins. Toxins cause cytotoxic damage of the host tissue. The complement system is thus activated relentlessly causing septic shock, acute respiratory distress syndrome and death.

$C^3$(101) represents three activating pathways (e.g., alternate, lectin-based and classical complement pathways) of the complement system. C3 (103) is a common end product of $C^3$. C3b (105) is an activated C3 with thioester bond removed. Factor D (107) is a serine protease activating protein of the alternate complement activating pathway. C3bBb (109) is a C3 convertase that flags foreign pathogens.

Factor H (111) is a complement regulatory protein that has been assigned a new role of recognizing self, host tissue, as per recent advances in immunology. Microbes pirate this protein to mask its identity as self. C3a–C5a (113) are activating intermediary complement products with host inflarmnatory actions (115). Entry of bacteria is facilitated through the surface receptors of CD4 macrophages (immature dendritic cells) (117). In the CD4 mature cells (119), the processed pathogens, through phagocytosis, express foreign signals by depositing peptide fragments in MHC 1 and MHC 11 grooves.

The CD 4 T cells (121) are cells of adaptive immunity that sense foreign signals according to "two signal hypothesis". Th 2 cells (123) are a sub-type of the CD 4 T cells, and are involved in humeral cellular responses. Ab (127) is an antibody that is formed by stimulation of B cells (125) by the Th 2 cells (123).

Figure 2:
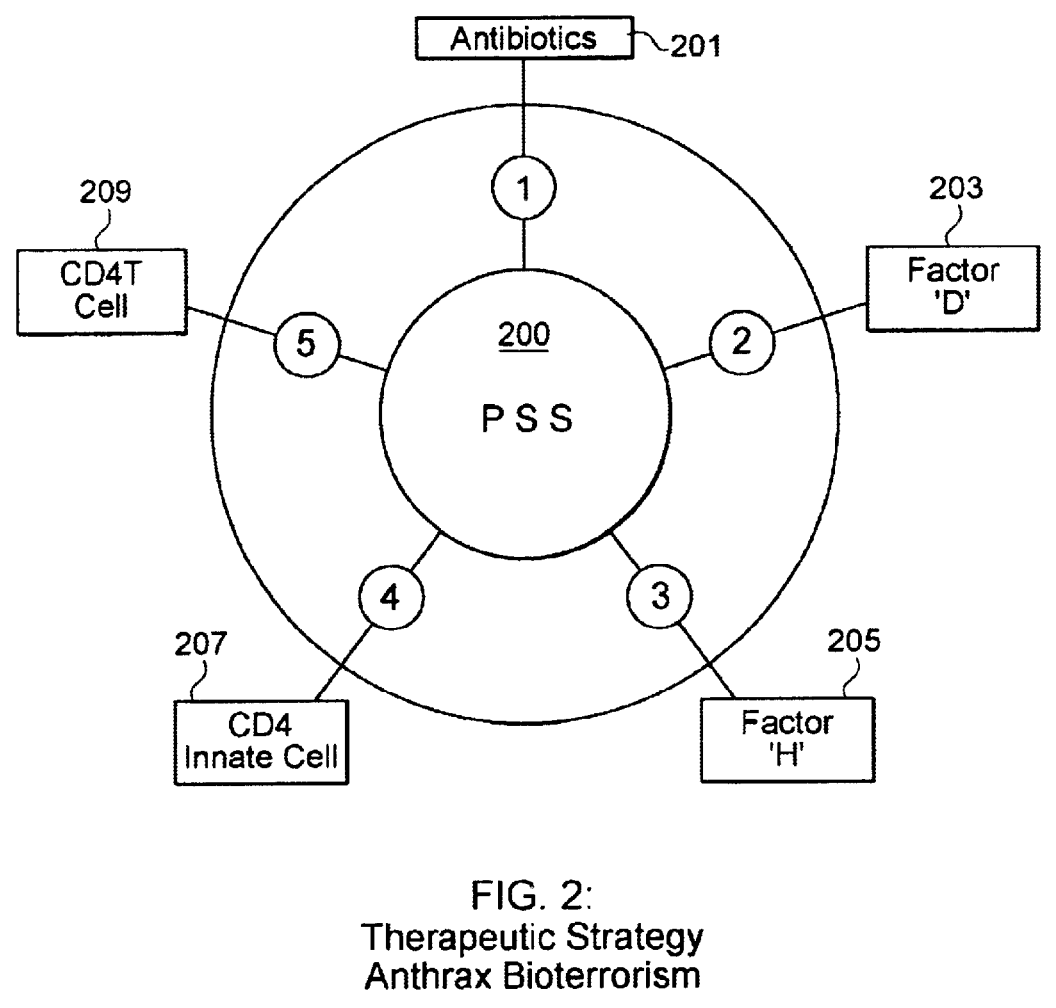

PSS is a low ionic strength synthetic polymer and has been used as a delivery vehicle for a large number of therapeutic compounds including ciprofloxacillin. (Moreau J. M., Green L. C., Engel L. S. et al. Effectiveness of ciprofloxacillin-polystyrene sulfonate (PSS), ciprofloxacin and ofloxacin in a staphylococcus keratitis model., Curr Eye Res, 1998; 17(8):808–12). One particular advantage is improved pharmacokinetics. This should be reflected in the steady state concentration, slow release of the drug, reduced side effects and toxicity. Reduced risk of resistance and reduced frequency of dosage should be the expected benefits. Combining this strategy with an appropriate immune modulation dosage of PSS (200) permits the targeting of Factor D (203), Factor H (205) and CD 4(207) cells as depicted in FIG. 2.

FIG. 2 is a diagram illustrating an exemplary therapeutic strategy for anthrax bio-terrorism according to an aspect of the present invention. Advantageously, using an appropriate immune modulation dosage of PSS (200) provides a five-fold targeting of anthrax, namely, in that combining PSS with antibiotics (201) provides an improvement in pharmacokinetics. In addition, Factor D cells (203) are targeted, which provides complement inhibition in septic shock, and also inhibits toxins, and Factor H cells (205) are targeted, which results in inhibition of immune invasion mechanisms. Further, humeral and cytotoxic immune responses are stimulated by the interaction of innate CD 4 cells (207) and CD 4 T cells (209).

PSS is an ion exchange resin with mean mesh size of about 50 microns. The fractionation of PSS with siever results in different fractions ranging from <20 microns to >105 microns. (Higaki M., Takase T., Igarashi R. et al. Enhancement of immune response to intranasal influenza HA vaccine by micro particle resin. Vaccine, 1998; Vol. 16 No. 7: 741–745). The immune modulation action of PSS on Factor D (203) and Factor h (205) is size independent. (Setoyama H., Inoue K., Iwata H. et al. The Potential of Anti-Complement Synthetic Sulfonic Polymers for Xenotransplantation. Transplantation Proceedings, 1998, 30: 67–70; Iwata H., Murakarni Y., Ikada Y. Control of complement activities for immunoisolation. Ann NY Acad Sci., 1999, 875:7–23; Date L, Miyoshi Y., Ono T. et al. Preliminary report of polymer-encapsulated dopamine-secreting cell grafting into the brain. Cell Transplantation, 1996, 5: S17–S19; Pascual M., Plastre O., Montdargent B. et al. Specific interactions of polystyrene biomaterials with Factor D of human complement Biomaterials. 1993, 14: 665–670). Thus, the first level of hierarchy and its modulation do not require size fractionation. CD 4 surface receptors, entry of bacteria and its flagging of MHC 1 and 11 receptors is the second level of hierarchy. The binding of polystyrene sulfonate and prevention of receptor functions is related to large size of polystyrene sulfonate. (Tan G. T., Wickramsinghe A., Verma S. et al. Sulfonic acid polymers are potent inhibitors of HIV-1 induced cytopathogenicity and the reverse transcriptases of both HIV-1 and HIV-2. Biochimica et Biophysica Acta, 1993, 1181(2):183–188; Anderson R A., Feathergill K., Diao X. et al. Evaluation of Poly(Styrene-4-Sulfonate) as a Preventive agent for Conception and Sexually transmitted diseases. J Androl 2000 November–December, 21(6): 862–875; Herold B. C, Bourne N.. Marcellino D. et al. Poly (Styrene-4-Sulfonate): An Effective Candidate Topical Antimicrobial for the Prevention of Sexually Transmitted Diseases. J Inf Dis 2000; 181:770–773). Thus, targeting of the second level of hierarchy can be done selectively by large size fractionation of polystyrene sulfonate. However, CD4 —CD 4 T cognate interactions, involving third level of hierarchy appears to depend on small molecular fraction of 20 microns or less. (Higaki M., Takase T., Igarashi R. et al. Enhancement of immune response to intranasal influenza HA vaccine by micro particle resin Vaccine, 1998, Vol. 16 No. 7: 741–745; Rhodes J., Chen H., Hall S. R. et al. Therapeutic potentiation of the immune system by co-stimulatory Schiff base forming drugs. Nature, 1995; 377(6544): 71–75). In a typical case, use of mixtures of different sizes of polystyrene sulfonate will therefore result in therapeutic reprogramming of the immune system. Indirectly, it boosts human defense system functioning by suppressing harmful complement activation in the first hierarchy. Bacterial infection and multiplication is prevented in the second level of hierarchy. At the third level of hierarchy immune responses are stimulated.

PSS is an endocrine drug originally introduced to medicine in 1935 and was formally approved in the USA in 1975. It has been used since 1975 for the therapy of high potassium. (Gerstman B. B. and Platt R. Uses of sodium polystyrene sulfonate in sorbitol in the United States, 1985–89. A. J. of Kidney Dis., 1991:15, No. 5, 619–620; Sodium polystyrene sulfonate, Martindale: The complete Drug Reference, $32^{nd}$ edition, edited by Parfitt K, Pharmaceutical Press, 1999: 995–996). Its ability to manipulate immune system, provide antibacterial and antitoxin effects have overlapping basic principles defined in endocrinology and immunology. Ideas and observations from clinics can be brought to the laboratory or to a more basic level of translational research hierarchy for further investigation as shown by the new applications of an established drug. PSS is a globally available drug at cost effective prices. (Sodium polystyrene sulfonate, Martindale: The complete Drug Reference, $32^{nd}$ edition, edited by Parfitt K., Pharmaceutical Press, 1999: 995–996). The mean approved dosage for the therapy of established indications, such as the therapy of high potassium, is 90 grams per day. Based on the immune modulation data reported in-vitro and in-vivo, the dose required appears to be less than a gram per day. The drug is preferably given in the dose of 5–10 mg/kg body weight. It is given as intravenous infusion in 250 ml–500 ml 0.85% saline over 2–3 hours to permit action of this drug at tissue or blood level where it is needed most. The frequency of doses could be once or twice a day. The mucosal safety data and blood contact safety data is readily available at this dosage. (Setoyama H., Inoue K., Iwata H. et al. The Potential of Anti-Complement Synthetic Sulfonic Polymers for Xenotransplantation. Transplantation Proceedings, 1998, 30: 67–70; Gerstman B. B. and Platt R. Uses of sodium polystyrene sulfonate in sorbitol in the United States, 1985–89. A. J. of Kidney Dis., 1991:15, No. 5, 619–620; Sodium polystyrene sulfonate, Martindale: The complete Drug Reference, $32^{nd}$ edition, edited by Parfitt K., Pharmaceutical Press, 1999: 995–996; Inaba S., Nibu K., Takano H. et al. Potassium adsorption filter for RBC transfusion: A phase iii clinical trial. Transfusion, 2000; 40: 1469–1474). Thus, combining this drug with an anti-microbial, such as, for example, ciprofloxacillin (Moreau J. M., Green L. C., Engel L. S. et al. Effectiveness of ciprofloxacillin-polystyrene sulfonate (PSS), ciprofloxacin and ofloxacin in a staphylococcus keratitis model., Curr Eye Res, 1998, 17(8):808–12), provides both anti-microbial and immune modulation therapy. The doses, frequency and duration are required to be determined based on outcome and monitoring of surrogate immune parameters related to the complement system and CD 4 counts, as well as routine parameters of infection. The oral dose may be added as desired based on clinical condition. According to the FDA, a new formulation represents the unlabeled use of an established drug. FDA regulation permits the use of such drug by a licensed physician in life threatening infections. According to FDA commissioner Charles C. Edwards, "Once the new drug is in pharmacy, the physician may, as part of the practice of medicine vary the condition of use from those approved in the package insert, without obtaining approval of the FDA" as per The Federal Registrar, Vol. 37, No. 158, Aug. 15, 1972. This is clearly restated in the April 1982 FDA Drug Bulletin Careful perusal of the current IND document also makes this clear. (Food and Drug Administration, HHS, Part 312-Investigational New Drug Application). As a therapy of anthrax, the present invention advantageously comprises a new application of an established drug that can be immediately used with zero tolerance to time. This will be life saving and prevent malpractice risk. The risk management involves carefully monitoring adverse effects in the patient and discontinuing the drug if adverse effects are observed.

Although illustrative embodiments of the present invention have been described herein with reference to the accompanying drawings, it is to be understood that the present invention is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A method of modulating an immune response in a host induced by pathogens comprising the steps of:
    providing polystyrene sulfonate in a dose of 5–10 mg per kg of body weight of the mammal;
    infusing the polystyrene sulfonate in a saline solution to form a polystyrene sulfonate infusion;
    dissolving ultra purified alginate into the polystyrene sulfonate infusion to form a polystyrene sulfonate and alginate infusion; and administering the polystyrene sulfonate and alginate infusion intravenously to the mammal, wherein the polystyrene sulfonate and alginate infusion provides immune modulation action on Factor D, Factor H and CD4 cells in the mammal.

2. The method of claim 1, wherein the polystyrene sulfonate and alginate infusion is administered intravenously to the mammal over a period of at least 2 hours.

3. The method of claim 1, wherein the polystyrene sulfonate is infused in 250 ml to 500 ml of a 0.85% saline solution.

4. The method of claim 1, further comprising the step of treating the coated polystyrene sulfonate with a gelling agent.

5. The method of claim 4, wherein the gelling agent comprises CaCl in 1–2% concentration.

6. The method of claim 1, wherein the step of providing further comprises providing a mixture of different size fractionations of polystyrene sulfonate.

7. The method of claim 6, wherein said mixture comprises at least one of a large molecular fractionation of polystyrene sulfonate greater than or equal to 100 microns and a small molecular fractionation of polystyrene sulfonate less than or equal to 20 microns.

8. A method of suppressing negative pathology caused by acute onset of complement system activation in a mammal exposed to pathogens, said pathogens releasing at least one of exotoxins and endotoxins in the mammal, and stimulating immune responses in said mammal, the method comprising the steps of:
    providing a mixture of different size fractionations of polystyrene sulfonate in a dose of 5–10 mg per kg of body weight of the mammal;
    infusing the mixture of polystyrene sulfonate in a saline solution to form a polystyrene sulfonate infusion;
    dissolving ultra purified alginate into the polystyrene sulfonate infusion to form a polystyrene sulfonate and alginate infusion; and
    administering the polystyrene sulfonate and alginate infusion intravenously to the mammal, wherein the polystyrene sulfonate and alginate infusion provides therapeutic immune modulation action on Factor D, Factor H and CD4 cells for inhibiting the acute complement system activation and stimulating immune responses in the mammal.

9. The method of claim 8, wherein the polystyrene sulfonate and alginate infusion is administered intravenously to the mammal over a period of at least 2 hours.

10. The method of claim 8, wherein the polystyrene sulfonate is infused in 250 ml to 500 ml of a 0.85% saline solution.

11. The method of claim 8, further comprising the step of treating the coated polystyrene sulfonate with a gelling agent.

12. The method of claim 11, wherein the gelling agent comprises CaCl in 1–2% concentration.

13. The method of claim 8, wherein after the administering step, further comprising the step of monitoring adverse effects in the host, wherein if adverse effects are detected, further comprising the step of discontinuing the administering of the polystyrene sulfonate and alginate infusion to the host.

14. The method of claim 8, wherein said mixture comprises at least one of a large molecular fractionation of polystyrene sulfonate greater than or equal to 100 microns and a small molecular fractionation of polystyrene sulfonate less than or equal to 20 microns.

* * * * *